US00PP36115P2

(12) United States Plant Patent
Bergman

(10) Patent No.: US PP36,115 P2
(45) Date of Patent: Sep. 17, 2024

(54) *MANDEVILLA* PLANT NAMED 'MANZ0029'

(50) Latin Name: ***Mandevilla sanderi* (Hemsl.) Woodson**
Varietal Denomination: MANZ0029

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/225,747

(22) Filed: Jul. 25, 2023

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — Dale Skalla

(57) ABSTRACT

A new *Mandevilla* plant named 'MANZ0029' particularly distinguished by its deep red to purplish red flowers, glossy and smooth dark green foliage, bushy plant habit with excellent branching and flower production and fast flowering response, good container and garden performance, known to be hardy to USDA Zone 9b.

1 Drawing Sheet

Latin name of the genus and species of the plant claimed: *Mandevilla sanderi* (Hemsl.) Woodson.

Varietal denomination: 'MANZ0029'.

BACKGROUND OF THE NEW PLANT

The present invention comprises a new *Mandevilla*, botanically known as *Mandevilla sanderi*, and hereinafter referred to by the variety name 'MANZ0029'.

'MANZ0029' is a product of a planned breeding program. The new cultivar has deep red to purplish red flowers, glossy and smooth dark green foliage, bushy plant habit with excellent branching and flower production and fast flowering response and good container and garden performance.

'MANZ0029' originates from a hybridization made in a controlled breeding program in Amatitlan, Guatemala. The pollinations were made in 2014.

The female parent was an unpatented, proprietary plant identified as 'DIP-252' and having approximately 10% larger sized bright red flowers, a more vigorous vigorous growth habit and larger foliage than 'MANZ0029'.

The male parent of 'MANZ0029' was an unpatented, proprietary plant identified as 'DIP-059', with approximately 10% smaller red flowers, smaller foliage, a more compact growth habit and earlier flowering response 'MANZ0029'.

The resulting seeds were sown in February 2015 and 'MANZ0029' was selected as one flowering plant within the progeny of the stated cross in January 2016 in a greenhouse in Gilroy, California.

The first act of asexual reproduction of 'MANZ0029' was accomplished when vegetative cuttings were propagated from the initial selection in March 2016 in a controlled environment in Gilroy, California.

BRIEF SUMMARY OF INVENTION

Horticultural examination of plants grown from cuttings of the plant initiated in March 2016 in Gilroy, California, and continuing thereafter, has demonstrated that the combination of characteristics as herein disclosed for 'MANZ0029' are firmly fixed and are retained through successive generations of asexual reproduction.

'MANZ0029' has not been observed under all possible environmental conditions. The phenotype may vary significantly with variations in environment such as temperature, light intensity and day length.

A Plant Breeder's Right for this cultivar was applied for in the European Union on May 16, 2023, No. 2023/1070. 'MANZ0029' has not been made publicly available prior to the effective filing date of this application, notwithstanding any disclosure that may have been made less than one year prior to the effective filing date of this application by the inventor or another who obtained 'MANZ0029' directly from the inventor.

The following traits have been repeatedly observed and are determined to be basic characteristics of the new variety. The combination of these characteristics distinguishes this *Mandevilla* as a new and distinct variety.

BRIEF DESCRIPTION OF THE PHOTOGRAPHS

The accompanying photographic drawings show typical flower and foliage characteristics of 'MANZ0029' with colors being as true as possible with an illustration of this type.

Figure 1:
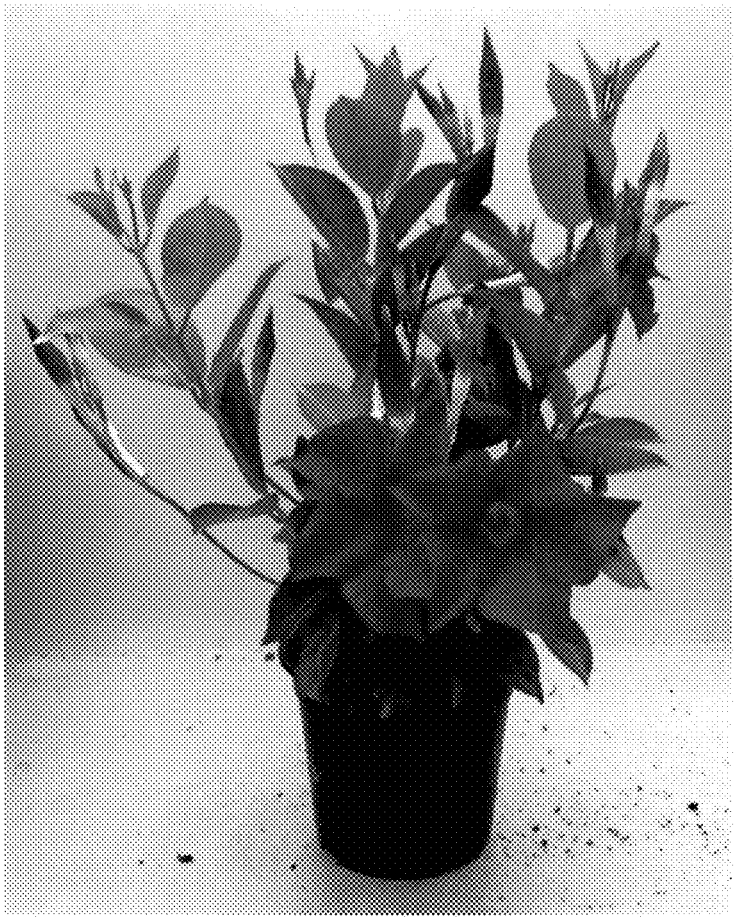
Figure 2:
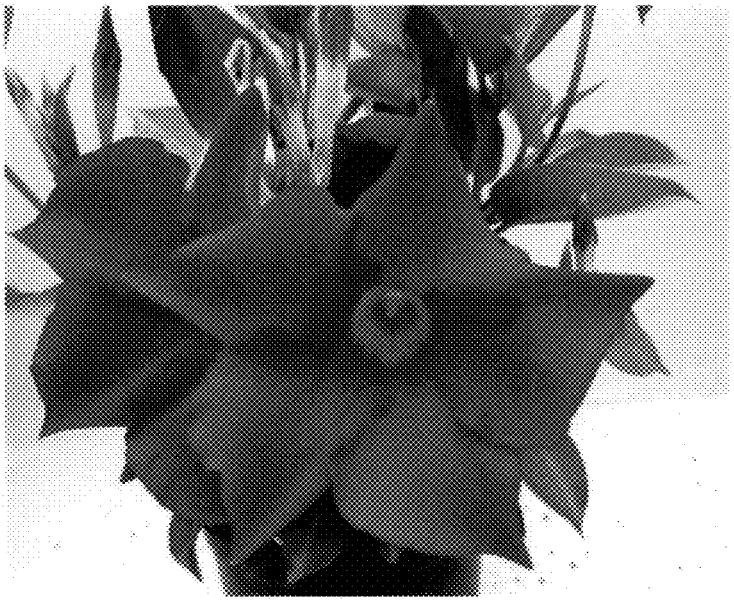

The photographic drawings show in FIG. 1, a flowering potted plant of the new variety, approximately 6 months old, taken in Andijk, The Netherlands in May 2023, and in FIG. 2, a close-up of a flower on a 6 month old plant taken in Andijk, The Netherlands in May 2023.

DETAILED BOTANICAL DESCRIPTION

The detailed botanical description was completed in July 2023 in Gilroy, California. The plants were growing in 14" pots out of doors in Gilroy, California. The plants were about 14 weeks in age.

TABLE 1

DIFFERENCES BETWEEN THE VARIETY 'MANZ0029' AND A SIMILAR VARIETY

| | 'MANZ0029' | 'Fisrix Dered', U.S. Plant Pat. No. 20,714 |
|---|---|---|
| Flower petals: | 0.5-0.8 cm wider | 0.5-0.8 cm more narrow |
| Flower length: | 1 cm longer | 1 cm shorter |
| Flowering response: | 2-3 weeks faster | 2-3 weeks slower |

Plant:

*Form, growth, and habit.*—Perennial or sub-shrub, herbaceous younger stems, woody at base of older stems, semi-upright, with slight tendency of developing vines depending on season and light intensity. Time for producing a commercial, flowering plant approximately is 18-20 weeks for one plant in a quart size container.

*Plant height.*—20 cm.

*Plant height (inflorescence included).*—21 cm.

*Plant width.*—17 cm.

Roots:

*Number of days to initiate roots.*—About 20-23 days at about 22 degrees C.

*Number of days to produce a rooted cutting plant.*—5 weeks at about 22 degrees C.

*Type.*—Fibrous, a little fleshy, free branching.

*Color.*—RHS 155D.

Foliage:

*Arrangement of leaves.*—Simple leaf, opposite and decussate.

*Immature leaf, color upper surface.*—RHS 137C.

*Immature leaf, color lower surface.*—RHS 138B.

*Mature leaf, color upper surface.*—RHS 139A.

*Mature leaf, color lower surface.*—RHS 137C.

*Length.*—7.1-8.0 cm.

*Width.*—3.6-5.3 cm.

*Shape.*—Ovate.

*Base shape.*—Rounded.

*Apex shape.*—Broadly acuminate.

*Margin.*—Entire.

*Texture, upper surface.*—Smooth, glossy, glabrous.

*Texture, lower surface.*—Smooth, glossy, glabrous.

*Pattern of leaf veins.*—Pinnate.

*Color of veins, upper surface.*—RHS 139D.

*Color of vein (midrib), lower surface.*—RHS 145C.

*Petiole color.*—RHS 138B.

*Length.*—0.9-1.2 cm.

*Diameter.*—0.2 cm.

*Petiole, texture.*—Glabrous.

Stem:

*Branching characteristics.*—Moderately free branching.

*Quantity of main branches per plant.*—4-5.

*Color of stem.*—RHS 138A.

*Length of stem.*—15-16 cm.

*Diameter (at about mid-point).*—0.25 cm.

*Length of internodes.*—1.2-2.3 cm.

*Stem, texture.*—Smooth and glabrous.

Inflorescence:

*Type of inflorescence.*—Raceme of several flowers, emerging from nodes of the stem.

*Number of flowers per inflorescence.*—6-9.

*Length.*—19 cm.

*Diameter.*—15 cm.

*Blooming habit.*—Continuously through the summer months.

*Quantity of flowers per plant.*—About 10 in various stages of development.

*Lastingness of individual blooms on the plant.*—Approximately 8-10 days, depending on temperature.

*Fragrance.*—Absent.

Peduncle:

*Color.*—Green, RHS 138A.

*Length.*—7.5-11.5 cm.

*Diameter.*—0.2 cm.

*Texture.*—Smooth, glabrous, somewhat glossy.

Bud (just before opening/showing color):

*Color.*—RHS 59A.

*Length.*—7.9 cm.

*Width.*—1.7 cm.

*Shape.*—Elongated, spindle shape.

Immature flower:

*Diameter.*—7.4 cm.

*Vertical diameter.*—About 6.5 cm.

*Color upper surface.*—RHS 60A with slight tones of RHS 59B.

*Color lower surface.*—RHS 59B with streaks of RHS 155D.

Mature flower:

*Shape.*—Funnelform, funnel shaped base, formed by 5 partly fused petals, with the petal lobes opening outwards, and a little overlapping.

*Flower, horizontal diameter.*—8.5 cm.

*Flower, vertical diameter.*—About 9.0 cm.

*Flower, diameter of the funnel.*—1.7 cm.

*Flower color, general.*—Red.

*Flower color, upper surface.*—RHS 60B with tones of RHS 60C and RHS 59B.

*Flower color, lower surface.*—RHS 59B with tones of RHS 59A and RHS 60C.

*Color of the funnel, inner side.*—Closest to RHS 171B with streaks of RHS 60A.

*Color of the funnel, outside.*—Closest to RHS 60B with streaks of RHS 61B.

*Petal, shape.*—Roughly ovate, asymmetric.

*Petal apex shape.*—Broadly acuminate.

*Petal base shape.*—Fused.

*Petal margin.*—Mainly entire and mildly undulate.

*Petal length, from the corolla opening.*—3.7 cm.

*Petal width, maximum.*—3.0 cm.

*Corolla, texture of upper surface.*—Glabrous, papillose.

*Corolla, texture of lower surface.*—Glabrous, papillose.

*Pedicel, color.*—RHS 138B.

*Length.*—1.6-2.4 cm.

*Diameter.*—0.2 cm.

*Pedicel, texture.*—Smooth, glabrous.

Calyx:

*Form.*—5 sepals, closely attached to the base of the flower.

*Color, visible outer surface.*—RHS 145A.

*Length.*—1.25 cm.

*Width.*—0.6 cm.

*Shape.*—Subulate.

*Apex shape.*—Acute.

*Base.*—Fused.

*Margins.*—Entire.

*Texture, upper surface.*—Glabrous.

Reproductive organs:

Gynoecium:

*Pistil.*—1, with a 5-lobed stigma.

*Style length.*—2.0 cm.

*Diameter.*—0.05 cm.

*Style color.*—RHS 149D.

*Stigma color.*—RHS 145B with 178C at the apex.

*Stigma shape.*—Five lobed.

*Ovary color.*—RHS 144B.

Androecium:

*Stamens.*—5, surrounding the style and stigma.

*Filaments.*—Fused with the base of the flower.

*Anther.*—Elongated.

*Anther color.*—RHS 164D.

*Anther length.*—1.0 cm.

*Color of pollen.*—RHS 159C.

*Pollen amount.*—Scarce.

Fertility/seed set: Has not been observed on this hybrid.

Disease/pest resistance: Has not been observed on this hybrid.

Plant hardiness: Known hardiness to USDA Zone 9b.

Heat tolerance: Known to be tolerant up to 45° C.

What is claimed is:

1. A new and distinct variety of *Mandevilla* plant named 'MANZ0029' substantially as illustrated and described herein.

* * * * *